United States Patent
Rollinger et al.

(10) Patent No.: US 7,785,821 B2
(45) Date of Patent: Aug. 31, 2010

(54) MEASUREMENT OF NICOTINAMDE N-METHYL TRANSFERASE IN DIAGNOSIS OF LUNG CANCER

(75) Inventors: Wolfgang Rollinger, Polling (DE); Marie Luise Hagmann, Penzberg (DE); Johann Karl, Peissenberg (DE); Theresa Kott, Munich (DE); Markus Roessler, Germering (DE); Michael Tacke, Munich (DE)

(73) Assignee: Roche Diagnostics Operations Inc., Indianapolis, IN (US)

( * ) Notice: Subject to any disclaimer, the term of this patent is extended or adjusted under 35 U.S.C. 154(b) by 0 days.

(21) Appl. No.: 12/362,584

(22) Filed: Jan. 30, 2009

(65) Prior Publication Data

US 2009/0263841 A1   Oct. 22, 2009

Related U.S. Application Data

(63) Continuation of application No. PCT/EP2007/006713, filed on Jul. 30, 2007.

(30) Foreign Application Priority Data

Aug. 1, 2006   (EP) ................................. 06015951

(51) Int. Cl.
    *C12Q 1/48* (2006.01)
(52) U.S. Cl. ....................................... 435/15; 435/7.23
(58) Field of Classification Search ................... 435/15, 435/7.23
    See application file for complete search history.

(56) References Cited

U.S. PATENT DOCUMENTS

| 2006/0024692 A1* | 2/2006 | Nakamura et al. | 435/6 |
| 2008/0020414 A1* | 1/2008 | Karl et al. | 435/15 |
| 2009/0176228 A1* | 7/2009 | Birse et al. | 435/6 |

FOREIGN PATENT DOCUMENTS

EP   2071337 A1 *  6/2009

OTHER PUBLICATIONS

Tomida M. et al. Serum Levels of NNMT in Patients with Lung Cancer. J Cancer Res Clin Oncol 135(9)1223-9, Sep. 2009.*
Nakagawa K. et al. N-Methylnicotinamide Level in the Blood after Nicotinamide Loading as Further Evidence for Malignant Tumor Burden. Japan J Cancer Research 82(11)1277-83, Nov. 1991.*

* cited by examiner

*Primary Examiner*—Ralph Gitomer
(74) *Attorney, Agent, or Firm*—Marilyn L. Amick

(57) ABSTRACT

The present invention relates to the assessment of lung cancer. It discloses the use of protein NNMT in the assessment of lung cancer. It also relates to a method for assessing lung cancer by measuring NNMT in vitro in a liquid sample derived from an individual. Measurement of NNMT can, e.g., be used in the early detection or in the follow-up of patients with lung cancer.

6 Claims, No Drawings

MEASUREMENT OF NICOTINAMDE N-METHYL TRANSFERASE IN DIAGNOSIS OF LUNG CANCER

RELATED APPLICATIONS

This application is a continuation of PCT/EP2007/006713 filed Jul. 30, 2007 and claims priority to EP 06015951.4 filed Aug. 1, 2006.

FIELD OF THE INVENTION

The present invention relates to a method aiding in the assessment of pulmonary or lung cancer (LC) and in particular in the assessment of non-small cell lung carcinoma (NSCLC). It discloses the use of the protein nicotinamide N-methyl transferase (NNMT) as a marker of LC, particularly NSCLC. Furthermore, it especially relates to a method for assessing lung cancer from a liquid sample, derived from an individual by measuring NNMT in said sample. Measurement of NNMT can, e.g., be used in the early detection of lung cancer or in the surveillance of patients who undergo surgery.

BACKGROUND OF THE INVENTION

Cancer remains a major public health challenge despite progress in detection and therapy. Amongst the various types of cancer, LC is a frequent cancer in the Western world and among the most frequent cause of cancer-related mortality. This is in large part due to the diagnostic gap for early detection of the disease. LC is largely asymptomatic in its early stages. The majority of all lung cancers is detected at a late stage when the disease has already become inoperable.

The majority of LC tumors can be divided into small cell lung carcinoma (SCLC) and non-small cell lung carcinoma (NSCLC). SCLC accounts for about 20-25% of all lung cancer cases. SCLC is an aggressive neuroendocrine type of LC and has a very poor prognosis even if detected in early stages. SCLC is rarely amenable to curative treatment by resection. Because of the speed with which the disease progresses, SCLC is generally categorized using only two stages, i.e., limited and extensive disease, rather than the more complex TNM staging system (see below). About 75-80% of LC cases are grouped into the class of NSCLC including squamous cell carcinoma (carcinoma=CA), adeno-CA (comprising the subclasses of acinar CA, papillary CA, bronchoalveolar tumor, solid tumor, and mixed subtypes), and large cell carcinoma (comprising the subclasses of giant cell tumors, clear cell CA, adenosquamous CA, and undifferentiated CA).

NSCLC, if detected at late stages, also has a very poor prognosis. The staging of cancer is the classification of the disease in terms of extent, progression, and severity. It groups cancer patients so that generalizations can be made about prognosis and the choice of therapy.

Today, the TNM system is the most widely used classification system based on the anatomical extent of cancer. It represents an internationally accepted, uniform staging system. There are three basic variables: T (the extent of the primary tumor), N (the status of regional lymph nodes) and M (the presence or absence of distant metastases). The TNM criteria are published by the UICC (International Union Against Cancer), in: TNM Classification of Malignant Tumours, fifth edition, Sobin, L. H. and Wittekind, Ch. (eds.), Wiley-Liss (1997), pp. 1803-1804)

Surgical resection of the primary tumor is widely accepted as the treatment of choice for early stage NSCLC. With the progression of NSCLC and, more specifically, the transition from stage IIIa (T3N1M0, T1N2M0, T2N2M0, T3N2M0) to IIIb (T4N0M0, T4N1M0, T4N2M0), a significant shift in the physician's approach is precipitated. However, if the cancer is detected during the more early stages (Ia-IIIa; preferably up to stage T3N1M0), the five-year survival rate varies between 35% and 80%. Detection at stage Ia ((T1N0M0); small tumor size, no metastasis) has evidently the best prognosis with a five-year survival of up to 80%.

Surgery is rarely, if ever, used in the management of stage IIIb-IV of NSCLC. Stage IV corresponds to distant metastasis, i.e., spread of the disease beyond the lungs and regional lymph nodes. The five-year survival rate in the later stages (III-IV) drops to between less than 1% and 15%.

What is especially important is that early diagnosis of NSCLC translates to a much better prognosis. Patients diagnosed as early as in stage Ia (T1N0M0), Ib (T2N0M0), IIa (T1N1M0), IIb, (T3N0M0), and IIIa (T3N1M0), if treated properly have an up to 80% chance of survival 5 years after diagnosis. This has to be compared to a 5-years survival rate of less than 1% for patients diagnosed once distant metastases are already present.

In the sense of the present invention early assessment of LC refers to an assessment at a tumor stage T1N0M0 or T1-3N0-1M0.

It is preferred that LC is assessed at stage T1-3N0-1M0 (=T1-3N0-M0).

Most lung cancers are detected when they become symptomatic. Current detection methods include chest x-ray, spiral computer tomography, sputum cytology and bronchioscopy. However, there is controversy regarding the suitability of these means for mass screenings.

A number of serum tumor markers for lung cancers are in clinical use. The soluble 30 kDa fragment of cytoceratin 19 (CYFRA 21-1), carcinoembryogenic antigen (CEA), neuron-specific enolase (NSE), and squamous cell carcinoma antigen (SCC) are the most prominent LC markers. However, none of them meets the criteria for sensitivity and specificity required for a screening tool (Thomas, L., Labor und Diagnose, TH Books Verlagsgesellschaft, Frankfurt/Main, Germany (2000)).

In order to be of clinical utility, a new diagnostic marker as a single marker should be comparable to other markers known in the art, or better. Or, a new marker should lead to a progress in diagnostic sensitivity and/or specificity either if used alone or in combination with one or more other markers, respectively. The diagnostic sensitivity and/or specificity of a test is best assessed by its receiver-operating characteristics, which will be described in detail below.

Whole blood, serum or plasma are the most widely used sources of sample in clinical routine. The identification of an early LC tumor marker that would aid in the reliable cancer detection or provide early prognostic information could lead to a method that would greatly aid in the diagnosis and in the management of this disease. Therefore, an urgent clinical need exists to improve the in vitro assessment of LC. It is especially important to improve the early diagnosis of LC, since for patients diagnosed early on chances of survival are much higher as compared to those diagnosed at a progressed stage of disease.

The clinical utility of biochemical markers in lung cancer has recently been reviewed (Duffy, M. J., Crit. Rev. Clin. Lab. Sci. 38 (2001) 225-262).

CYFRA 21-1 is currently regarded to be the best of the presently known tumor markers for lung cancer. Even though not organ-specific it is predominantly found in lung tissue. Sensitivity of CYFRA 21-1 for lung cancer is described to be between 46-61% at a specificity of 95% towards other benign lung diseases. Increased serum levels of CYFRA 21-1 are also associated with pronounced benign liver diseases, renal insufficiency and invasive bladder cancer. CYFRA 21-1 testing is recommended for postoperative therapy surveillance.

CEA belongs to the group of carcinofetal antigens usually produced during embryogenesis. CEA is not organ-specific and predominantly used for monitoring of colorectal cancer.

Besides malignancies, also several benign diseases such as cirrhosis, bronchitis, pancreatitis and autoimmune diseases are associated with increased CEA serum levels. At 95% specificity towards benign lung diseases its sensitivity for lung cancer is reported to be 29-44%. A preferred use of CEA is therapy surveillance of lung cancer.

NSE is a tumor marker for SCLC. Generally, increased NSE serum levels are found in association with neuroectodermal and neuroendocrine tumors. Increased serum levels are also found in patients with benign lung diseases and cerebral diseases, such as meningitis or other inflammatory diseases of the brain, and traumatic injuries to the head. While sensitivity for SCLC at 95% specificity is reported to be 60-87%, performance of NSE testing for NSCLC is poor (7-25%). NSE is recommended for therapy surveillance of SCLC.

SCC was originally identified in squamous cell CA of the cervix. The sensitivity of SCC for LC in general is low (18-27%). Therefore, SCC testing is regarded to be not suitable for screening. However, due to a higher sensitivity for squamous cell CA, a preferred use for SCC is therapy surveillance, even though CYFRA 21-1 generally performs better.

With respect to marker profiles and aiming at improved diagnosis of lung cancer, a method was published (Schneider, J. et al., Int. J. Clin. Oncol. 7 (2002) 145-151) using fuzzy logic based classification algorithms to combine serum levels of CYFRA 21-1, NSE and C-reactive protein (CRP) which is a general inflammation marker. The authors report a sensitivity of 92% at a specificity of 95%.

It was the task of the present invention to investigate whether a biochemical marker can be identified which may be used in assessing LC.

Surprisingly, it has been found that use of the marker NNMT can at least partially overcome some of the problems of the markers presently known in the state of the art.

SUMMARY OF THE INVENTION

The present invention relates to a method for assessing lung cancer in vitro comprising measuring in a sample the concentration of NNMT, and using the concentration determined in the assessment of lung cancer. Surprisingly it could be established that an increased level of NNMT in a sample is for example indicative for the presence of lung cancer in an individual.

The present invention is also directed to a method for assessing LC in vitro by biochemical markers, comprising measuring in a sample the concentration of NNMT and of one or more other marker of LC and using the concentrations determined in the assessment of LC. It is preferred that the one or more other marker of LC is selected from the group consisting of CYFRA 21-1, CEA, NSE, and SCC.

The present invention, in a preferred embodiment, also relates to the use of a marker panel comprising at least NNMT and CYFRA 21-1 in the assessment of LC.

The present invention also relates to the use of a marker panel comprising at least NNMT and CEA in the assessment of LC.

The present invention also relates to the use of a marker panel comprising at least NNMT and SCC in the assessment of LC.

In a preferred embodiment the present invention relates to a method for assessing lung cancer in vitro comprising measuring in a sample the concentration of a) NNMT, b) optionally one or more other marker of lung cancer, and c) using the concentrations determined in step (a) and optionally step (b) in the assessment of lung cancer.

DETAILED DESCRIPTION OF THE INVENTION

NNMT (nicotinamide N-methyl transferase, EC 2.1.1.1) catalyzes the N-methylation of nicotinamide and other pyridines. The protein NNMT (Swiss-PROT: P40261) is characterized by the sequence given in SEQ ID NO: 1. NNMT has an apparent molecular weight of 29.6 kDa and an isoelectric point of 5.56.

NNMT activity is important for biotransformation of many drugs and xenobiotic compounds. The protein has been reported to be predominantly expressed in liver and is located in the cytoplasm. NNMT has been cloned from cDNA from human liver and contained a 792-nucleotide open reading frame that encoded a 264-amino acid protein with a calculated molecular, mass of 29.6 kDa (Aksoy, S. et al., J. Biol. Chem. 269 (1994) 14835-14840). Little is known in the literature about a potential role of the enzyme in human cancer. In one paper, increased hepatic NNMT enzymatic activity was reported as a marker for cancer cachexia in mice (Okamura, A. et al., Jpn. J. Cancer Res. 89 (1998) 649-656). In a recent report, down-regulation of the NNMT gene in response to radiation in radiation sensitive cell lines was demonstrated (Kassem, H., et al., Int. J. Cancer 101 (2002) 454-460). In US 2006/0024692 the NNMT m-RNA-level was found to be lower in non-small cell lung carcinoma cells compared with non-cancerous tissue. WO 02/082076 describes NNMT protein as a marker for subtypes of renal carcinoma.

As used herein, each of the following terms has the meaning associated with it in this section.

The articles "a" and "an" are used herein to refer to one or to more than one (i.e., to at least one) of the grammatical object of the article. By way of example, "a marker" means one marker or more than one marker.

The term "marker" or "biochemical marker" as used herein refers to a molecules to be used as a target in the analysis of a patient sample. Examples of such molecular targets are proteins or polypeptides themselves as well as antibodies to such targets as present in a sample. The expression "one or more" denotes 1 to 20, preferably 1 to 10, preferably 1 to 5, more preferred 3 or 4.

Proteins or polypeptides used as a marker in the present invention are contemplated to include naturally occurring variants of said protein as well as naturally occurring fragments or complexes of said protein or said variant, in particular immunologically detectable fragments or complexes, respectively.

As obvious to the skilled artisan, the present invention shall not be construed to be limited to the measurement of the full-length protein NNMT of SEQ ID NO: 1. Physiological fragments of NNMT can also be measured and used as a marker for lung cancer while practicing the present invention. Immunologically detectable fragments preferably comprise at least 6, 7, 8, 10, 12, 15, or 20 contiguous amino acids of said marker polypeptide. One of skill in the art would recognize that proteins which are released by cells or present in the extracellular matrix may be damaged, e.g., during inflammation, and could become degraded or cleaved into such fragments. As the skilled artisan will appreciate, NNMT or fragments thereof may also be present as part of a complex. Such complex also may be used as a marker in the sense of the present invention. In addition, or in the alternative the NNMT polypeptide may carry a post-translational modification, preferably a glycosylation, acylation, and/or a phosphorylation, and such modified NNMT may also serve as a marker of LC.

The term "assessing lung cancer" is used to indicate that the method according to the present invention will (alone or together with other markers or variables, e.g., the criteria set forth by the UICC (see above)) e.g., aid the physician to establish or confirm the absence or presence of LC or aid the physician in the prognosis, the detection of recurrence (follow-up of patients after surgery) and/or the monitoring of treatment, especially of chemotherapy.

The term "sample" as used herein refers to a biological sample obtained for the purpose of evaluation in vitro. In the methods of the present invention, the sample or patient sample preferably may comprise any body fluid. Preferred samples are whole blood, serum, plasma, bronchial lavage or sputum, respectively, with plasma or serum being most preferred.

The inventors of the present invention have surprisingly been able to detect the marker NNMT in a significant percentage of samples derived from patients with LC. Even more surprising they have been able to demonstrate that the presence of NNMT in such liquid sample obtained from an individual can be used in the assessment of lung cancer.

In a preferred embodiment the present invention relates to a method for assessing LC by measuring in a sample the concentration of NNMT and using the concentration determined in the assessment of LC.

As the skilled artisan will appreciate, any such measurement is made in vitro. The patient sample is discarded afterwards. The patient sample is solely used for the in vitro diagnostic method of the invention and the material of the patient sample is not transferred back into the patient's body. Typically, the sample is a liquid sample, e.g., whole blood, serum, or plasma.

As the skilled artisan will appreciate from the examples described, NNMT has been identified by measurement in an immunoassay as a marker which is useful in the diagnosis of LC, alternative ways may be used to reach a result comparable to the achievements of the present invention. The marker protein NNMT may be detected by any appropriate means and used as a marker of LC. Such preferred appropriate means comprise the detection of NNMT by an immunoassay procedure, by any other form of binding assay, by measurement of its enzymatic activity, by liquid chromatography, especially high performance liquid chromatography, by electrophoresis, especially SDS-PAGE combined with Western Blotting and by mass spectroscopy.

The ideal scenario for diagnosis would be a situation wherein a single event or process would cause the respective disease as, e.g., in infectious diseases. In all other cases correct diagnosis can be very difficult, especially when the etiology of the disease is not fully understood as is the case for LC. As the skilled artisan will appreciate, no biochemical marker, for example in the field of LC, is diagnostic with 100% specificity and at the same time 100% sensitivity for a given disease. Rather, biochemical markers e.g., CYFRA 21-1, CEA, NSE, SCC, or as shown here NNMT can be used to assess with a certain likelihood or predictive value the presence or absence of a disease. Therefore in routine clinical diagnosis, generally various clinical symptoms and biological markers are considered together in the diagnosis, treatment and management of the underlying disease.

Biochemical markers can either be determined individually or in a preferred embodiment of the invention they can be measured simultaneously using a chip or a bead based array technology. The concentrations of the biomarkers are then either interpreted independently using an individual cut-off for each marker or they are combined for interpretation.

In a further preferred embodiment the assessment of LC according to the present invention is performed in a method comprising measuring in a sample the concentration of a) NNMT, b) one or more other marker of lung cancer, and c) using the concentration determined in step (a) and step (b) in the assessment of lung cancer. As obvious to the skilled artisan the measurement of NNMT and the measurement of the one or more other marker of lung cancer can be made alternatively from the same aliquot of a sample or from different aliquots According to the data shown in the Examples, the marker NNMT, both in the univariate analysis as well as in the multivariate analysis performed, has (at a specificity of about 95%) a remarkable sensitivity for LC of almost 50% and in this respect was found comparable or even superior as compared to other LC markers investigated. In the assessment of LC the marker NNMT will be of advantage in one or more of the following aspects: screening; diagnostic aid; prognosis; monitoring of therapy such as chemotherapy, radiotherapy, and immunotherapy.

Screening

Screening is defined as the systematic application of a test to identify individuals at sufficient risk of suffering from LC to benefit from further investigation or direct preventive action, among persons who have not sought medical attention on account of symptoms of LC.

As the data given in the Examples section demonstrate NNMT alone will not suffice to allow for a general screening e.g., of the at risk population for LC. Most likely no single biochemical marker in the circulation will ever meet the sensitivity and specificity criteria required for screening purposes. Rather it has to be expected that a marker panel will have to be used in LC screening. The data established in the present invention indicate that the marker NNMT will form an integral part of a marker panel appropriate for screening purposes. The present invention therefore relates to the use of NNMT as one marker of a LC marker panel for LC screening purposes. An increased level of NNMT is indicative for the presence of LC. The present data further indicate that certain combinations of markers will be advantageous in the screening for LC. Therefore the present invention also relates to the use of a marker panel comprising NNMT and CYFRA 21-1, or of a marker panel comprising NNMT and CEA, or of a marker panel comprising NNMT and NSE, or of a marker panel comprising NNMT and SCC or of a marker panel comprising NNMT and two markers selected from the group consisting of CYFRA 21-1, CEA, NSE, and SCC, for the purpose of screening for LC.

Diagnostic Aid

Markers may either aid the differential diagnosis of benign vs. malignant disease in a particular organ, or help distinguish between different histological types of a tumour. As reported by Molina, R. et al., Tumor Biol. 24 (2003) 209-218, CEA, CA 125, CYFRA 21-1, SSC and NSE were used as serum markers to aid histological diagnosis of LC. The results of that study also indicate that among the markers tested CYFRA 21-1 is the most sensitive marker in lung cancer but with no relationship to histology.

Since NNMT as a single marker according to the data of the present invention might be superior to other LC markers like CEA or NSE it has to be expected that NNMT will be used as a diagnostic aid, especially by establishing a baseline value before surgery. The present invention thus also relates to the use of NNMT for establishing a baseline value before surgery for LC.

Prognosis

Prognostic indicators can be defined as clinical, pathological, or biochemical features of cancer patients and their tumours that forecast disease outcome. Their main use is to help rationally plan patient management, i.e., avoid undertreatment of aggressive disease and overtreatment of indolent disease. Molina R. et al., Tumor Biol. (2003) 24:209-218 evaluated the prognostic value of CEA, CA 125, CYFRA 21-1, SSC and NSE in NSCLC. E.g., overall survival of patients was assessed, whereby abnormal serum levels of the markers NSE, CEA, and LDH (lactate dehydrogenase) appeared to indicate shorter survival.

As NNMT alone significantly contributes to the differentiation of LC patients from healthy controls, it has to be expected that it will aid in assessing the prognosis of patients suffering from LC. The level of preoperative NNMT will most likely be combined with one or more other marker for LC and/or the TNM staging system. In a preferred embodiment NNMT is used in the prognosis of patients with LC.

Monitoring of Chemotherapy

Merle, P. et al., Int. J. of Biological Markers 19 (2004) 310-315 have evaluated CYFRA 21-1 serum level variations in patients with locally advanced NSCLC treated with induction chemotherapy. They conclude that early monitoring of CYFRA 21-1 serum levels may be a useful prognostic tool for tumor response and survival in stage III NSCLC patients. In addition, reports have described the use of CEA in monitoring the treatment of patients with LC (Fukasawa, T. et al., Gan to Kagaku Ryoho. Cancer & Chemotherapy 13 (1986) 1862-1867 (written in Japanese); Zhang, H. et al., Shandong Yike Daxue Xuebao 39 (2001) 537-538, 541 (written in Chinese)). Most of these were retrospective, non-randomized and contained small numbers of patients. As in the case of the studies with CYFRA 21-1 the CEA studies suggested: a) that patients with a decrease in CEA levels while receiving chemotherapy generally had a better outcome than those patients whose CEA levels failed to decrease and (b) for almost all patients, increases in CEA levels were associated with disease progression.

Due to the data shown in the example section, it has to be expected that NNMT will be at least as good a marker for monitoring of chemotherapy as CYFRA 21-1 or CEA. The present invention therefore also relates to the use of NNMT in the monitoring of LC patients under chemotherapy.

Follow-Up

A large portion of LC patients who undergo surgical resection aimed at complete removal of cancerous tissue, later develop recurrent or metastatic disease (Wagner, H., Chest 117 (2000) 110-116; Buccheri, G. et al., Ann. Thorac. Surg. 75 (2003) 973-980). Most of these relapses occur within the first 2-3 years after surgery. Since recurrent/metastatic disease is invariably fatal, considerable research has focused on LC identification at an early and thus potentially treatable stage.

Consequently, many LC patients undergo a postoperative surveillance program which frequently includes regular monitoring with CEA. Serial monitoring with CEA one year after surgical resection has been shown to detect an early postoperative recurrent/metastatic disease with a sensitivity of approximately of 29%, specificity of approximately 97%, even in the absence of suspicious symptoms or signs (Buccheri, G. et al., Ann. Thorac. Surg. 75 (2003) 973-980). Thus, the follow-up of patients with LC after surgery is one of the most important fields of use for an appropriate biochemical marker. Due to the high sensitivity of NNMT in the LC patients investigated it is expected that NNMT alone or in combination with one or more other marker will be of great help in the follow-up of LC patients, especially in LC patients after surgery. The use of a marker panel comprising NNMT and one or more other marker of LC in the follow-up of LC patients represents a further preferred embodiment of the present invention.

The present invention in a preferred embodiment relates to the use of NNMT in the diagnostic field of LC or in the assessment of LC, respectively.

In yet a further preferred embodiment the present invention relates to the use of NNMT as a marker molecule for lung cancer in combination with one or more marker molecules for lung cancer in the assessment of lung cancer from a liquid sample obtained from an individual.

Thus, a preferred embodiment of the present invention is the use of NNMT as a marker molecule for lung cancer in combination with one or more marker molecules for lung cancer in the assessment of lung cancer from a liquid sample obtained from an individual. Preferred selected other LC markers with which the measurement of NNMT may be combined are CYFRA 21-1, CEA, NSE, and SCC. Yet further preferred the marker panel used in the assessment of LC comprises NNMT and at least one other marker molecule selected from the group consisting of CYFRA 21-1 and CEA.

As the skilled artisan will appreciate there are many ways to use the measurements of two or more markers in order to improve the diagnostic question under investigation. In a quite simple, but nonetheless often effective approach, a positive result is assumed if a sample is positive for at least one of the markers investigated. This may e.g., the case when diagnosing an infectious disease, like AIDS.

Frequently, however, the combination of markers is evaluated. Preferably the values measured for markers of a marker panel, e.g., for CYFRA and CEA, are mathematically combined and the combined value is correlated to the underlying diagnostic question. Marker values may be combined by any appropriate state of the art mathematical method. Well-known mathematical methods for correlating a marker combination to a disease employ methods like, discriminant analysis (DA) (i.e., linear-, quadratic-, regularized-DA), Kernel Methods (i.e., SVM), Nonparametric Methods (i.e., k-Nearest-Neighbor Classifiers), PLS (Partial Least Squares), Tree-Based Methods (i.e., Logic Regression, CART, Random Forest Methods, Boosting/Bagging Methods), Generalized Linear Models (i.e., Logistic Regression), Principal Components based Methods (i.e., SIMCA), Generalized Additive Models, Fuzzy Logic based Methods, Neural Networks and Genetic Algorithms based Methods. The skilled artisan will have no problem in selecting an appropriate method to evaluate a marker combination of the present invention. Preferably the method used in correlating the marker combination of the invention, e.g., to the absence or presence of LC is selected from DA (i.e., Linear-, Quadratic-, Regularized Discriminant Analysis), Kernel Methods (i.e., SVM), Nonparametric Methods (i.e., k-Nearest-Neighbor Classifiers), PLS (Partial Least Squares), Tree-Based Methods (i.e., Logic Regression, CART, Random Forest Methods, Boosting Methods), or Generalized Linear Models (i.e., Logistic Regression). Details relating to these statistical methods are found in the following references: Ruczinski, I. et al., J. of Computational and Graphical Statistics 12 (2003) 475-511; Friedman, J. H., J. of the American Statistical Association 84 (1989) 165-175; Hastie, T. et al., The Elements of Statistical Learning, Springer Series in Statistics (2001); Breiman, L. et al., Classification and Regression Trees, Wadsworth International Group, Belmont, Calif. (1984); Breiman, L., Random Forests, Machine Learning, 45 (2001) 5-32; Pepe, M. S., The Statistical Evaluation of Medical Tests for Classification and Prediction, Oxford Statistical Science Series, 28 (2003); and Duda, R. O. et al., Pattern Classification, Wiley Interscience, 2nd edition (2001).

It is a preferred embodiment of the invention to use an optimized multivariate cut-off for the underlying combination of biological markers and to discriminate state A from state B, e.g., diseased from healthy. In this type of analysis the markers are no longer independent but form a marker panel. It could be established that combining the measurements of NNMT with those of CYFRA 21-1 or CEA, respectively, does significantly improve the diagnostic accuracy for LC as compared to healthy controls.

Accuracy of a diagnostic method is best described by its receiver-operating characteristics (ROC) (see especially Zweig, M. H. and Campbell, G., Clin. Chem. 39 (1993) 561-577). The ROC graph is a plot of all of the sensitivity/specificity pairs resulting from continuously varying, the decision thresh-hold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease or benign versus malignant disease.

In each case, the ROC plot depicts the overlap between the two distributions by plotting the sensitivity versus 1—specificity for the complete range of decision thresholds. On the y-axis is sensitivity, or the true-positive fraction [defined as (number of true-positive test results)/(number of true-positive+number of false-negative test results)]. This has also been referred to as positivity in the presence of a disease or condition. It is calculated solely from the affected subgroup. On the x-axis is the false-positive fraction, or 1—specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One convenient goal to quantify the diagnostic accuracy of a laboratory test is to express its performance by a single number. Such an overall parameter, e.g., is the so-called "total error" or alternatively the "area under the curve=AUC". The most common global measure is the area under the ROC plot. By convention, this area is always $\geq 0.5$ (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

Combining measurements of NNMT with other markers like CYFRA 21-1 or CEA, or with other markers of LC yet to be discovered, NNMT leads and will lead, respectively, to further improvements in assessment of LC.

The combination of the two markers NNMT and CYFRA 21-1 significantly improves the diagnostic accuracy for LC. The combination of the two markers NNMT and CEA also significantly improves the diagnostic accuracy for LC.

In a preferred embodiment the present invention relates to a method for improving the diagnostic accuracy for LC versus healthy controls by measuring in a sample the concentration of at least NNMT and CYFRA 21-1, CEA, NSE, or SCC, respectively and correlating the concentrations determined to the presence or absence of LC, the improvement resulting in more patients being correctly classified as suffering from LC versus healthy controls as compared to a classification based on any single marker investigated alone.

In a preferred method according to the present invention at least the concentration of the biomarkers NNMT and CYFRA 21-1, respectively, is determined and the marker combination is used in the assessment of LC.

In a further preferred method according to the present invention at least the concentration of the biomarkers NNMT and CEA, respectively, is determined and the marker combination is used in the assessment of LC.

In yet a further preferred method according to the present invention at least the concentration of the biomarkers NNMT, CYFRA 21-1, and CEA, respectively, is determined and the marker combination is used in the assessment of LC.

In yet a further preferred method according to the present invention at least the concentration of the biomarkers NNMT, CYFRA 21-1, and SCC, respectively, is determined and the marker combination is used in the assessment of LC.

The following examples are provided to aid the understanding of the present invention, the true scope of which is set forth in the appended claims. It is understood that modifications can be made in the procedures set forth without departing from the spirit of the invention.

SPECIFIC EMBODIMENTS

Example 1

Generation of Antibodies to the Lung Cancer Marker Protein NNMT

Polyclonal antibody to the lung cancer marker protein NNMT was generated for further use of the antibody in the measurement of serum and plasma and blood levels of NNMT by immunodetection assays, e.g., Western Blotting and ELISA.

Recombinant Protein Expression in E. coli.

In order to generate antibodies to NNMT, recombinant expression of the protein was performed for obtaining immunogens. The expression was done applying a combination of the RTS 100 expression system and expression in E. coli. In a first step, the DNA sequence was analyzed and recommendations for high yield cDNA silent mutational variants and respective PCR-primer sequences were obtained using the "ProteoExpert RTS E. coli HY" system. This is a commercial web based service (www.proteoexpert.com). Using the recommended primer pairs, the "RTS 100 E. coli Linear Template Generation Set, His-tag" (Roche Diagnostics GmbH, Mannheim, Germany, Cat. No. 3186237) system to generate linear PCR templates from the cDNA and for in-vitro transcription and expression of the nucleotide sequence coding for the NNMT protein was used. For Western-blot detection and later purification, the expressed protein contained a His-tag. The best expressing variant was identified. All steps from PCR to expression and detection were carried out according to the instructions of the manufacturer. The respective PCR product, containing all necessary T7 regulatory regions (promoter, ribosomal binding site and T7 terminator) was cloned into the pBAD TOPO vector (Invitrogen, Karlsruhe, Germany, Cat. No. K 4300/01) following the manufacturer's instructions. For expression using the T7 regulatory sequences, the construct was transformed into E. coli BL 21 (DE 3) (Studier, F. W. et al., Methods Enzymol. 185 (1990) 60-89) and the transformed bacteria were cultivated in a 1 l batch for protein expression.

Purification of His-NNMT fusion protein was done following standard procedures on a Ni-chelate column. Briefly, 1 l of bacteria culture containing the expression vector for the His- NNMT fusion protein was pelleted by centrifugation. The cell pellet was resuspended in lysis buffer, containing phosphate, pH 8.0, 7 M guanidium chloride, imidazole and thioglycerole, followed by homogenization using a ULTRA-TURRAX (Janke & Kunkel GmbH). Insoluble material was pelleted by high speed centrifugation and the supernatant was applied to a Ni-chelate chromatographic column. The column was washed with several bed volumes of lysis buffer followed by washes with buffer, containing phosphate, pH 8.0 and urea. Finally, bound antigen was eluted using a phosphate buffer containing SDS under acid conditions.

Generation of Polyclonal Antibodies a) Immunization

For immunization, a fresh emulsion of the protein solution (100 µg/ml protein NNMT) and complete Freund's adjuvant at the ratio of 1:1 was prepared. Each rabbit was immunized with 1 ml of the emulsion at days 1, 7, 14 and 30, 60 and 90. Blood was drawn and resulting anti-NNMT serum used for further experiments as described in examples 3 and 4.

b) Purification of IgG (Immunoglobulin G) from Rabbit Serum by Sequential Precipitation with Caprylic Acid and Ammonium Sulfate One volume of rabbit serum was diluted with 4 volumes of acetate buffer (60 mM, pH 4.0). The pH was adjusted to 4.5 with 2 M Tris-base. Caprylic acid (25 µl/ml of diluted sample) was added drop-wise under vigorous stirring. After 30 min the sample was centrifuged (13 000×g, 30 min, 4° C.), the pellet discarded and the supernatant collected. The pH of the supernatant was adjusted to 7.5 by the addition of 2 M Tris-base and filtered (0.2 µm).

The immunoglobulin in the supernatant was precipitated under vigorous stirring by the drop-wise addition of a 4 M ammonium sulfate solution to a final concentration of 2 M. The precipitated immunoglobulins were collected by centrifugation (8000×g, 15 min, 4° C.).

The supernatant was discarded. The pellet was dissolved in 10 mM $NaH_2PO_4$/NaOH, pH 7.5, 30 mM NaCl and exhaustively dialyzed. The dialysate was centrifuged (13 000×g, 15 min, 4° C.) and filtered (0.2 µm).

Biotinylation of Polyclonal Rabbit IgG

Polyclonal rabbit IgG was brought to 10 mg/ml in 10 mM $NaH_2PO_4$/NaOH, pH 7.5, 30 mM NaCl. Per ml IgG solution 50 µl Biotin-N-hydroxysuccinimide (3.6 mg/ml in DMSO) were added. After 30 min at room temperature, the sample was chromatographed on Superdex 200 (10 mM $NaH_2PO_4$/NaOH, pH 7.5, 30 mM NaCl). The fraction containing biotinylated IgG were collected. Monoclonal antibodies have been biotinylated according to the same procedure.

Digoxygenylation of Polyclonal Rabbit IgG

Polyclonal rabbit IgG was brought to 10 mg/ml in 10 mM $NaH_2PO_4$/NaOH, 30 mM NaCl, pH 7.5. Per ml IgG solution 50 µl digoxigenin-3-O-methylcarbonyl-ε-aminocaproic acid-N-hydroxysuccinimide ester (Roche Diagnostics, Mannheim, Germany, Cat. No. 1 333 054) (3.8 mg/ml in DMSO) were added. After 30 min at room temperature, the sample was chromatographed on Superdex® 200 (10 mM $NaH_2PO_4$/NaOH, pH 7.5, 30 mM NaCl). The fractions containing digoxigenylated IgG were collected. Monoclonal antibodies have been labeled with digoxigenin according to the same procedure.

Example 2

ELISA for the measurement of NNMT in Human Serum and Plasma Samples

For detection of NNMT in human serum or plasma, a sandwich ELISA was developed. For capture and detection of the antigen, aliquots of the anti-NNMT polyclonal antibody (see Example 2) were conjugated with biotin and digoxygenin, respectively.

Streptavidin-coated 96-well microtiter plates were incubated with 100 µl biotinylated anti-NNMT polyclonal antibody for 60 min at 10 µg/ml in 10 mM phosphate, pH 7.4, 1%. BSA, 0.9% NaCl and 0.1% TWEEN 20 (ICI Americas Inc.). After incubation, plates were washed three times with 0.9% NaCl, 0.1% TWEEN 20. Wells were then incubated for 2 h with either a serial dilution of the recombinant protein (see Example 2) as standard antigen or with diluted plasma samples from patients. After binding of NNMT, plates were washed three times with 0.9% NaCl, 0.1% TWEEN 20. For specific detection of bound NNMT, wells were incubated with 100 µl of digoxygenylated anti-NNMT polyclonal antibody for 60 min at 10 µg/ml in 10 mM phosphate, pH 7.4, 1% BSA, 0.9% NaCl and 0.1% TWEEN 20. Thereafter, plates were washed three times to remove unbound antibody. In a next step, wells were incubated with 20 mU/ml anti-digoxigenin-POD conjugates (Roche Diagnostics GmbH, Mannheim, Germany, Catalog No. 1633716) for 60 min in 10 mM phosphate, pH 7.4, 1% BSA, 0.9% NaCl and 0.1% TWEEN 20. Plates were subsequently washed three times with the same buffer. For detection of antigen-antibody complexes, wells were incubated with 100 µl ABTS solution (Roche Diagnostics GmbH, Mannheim, Germany, Catalog No. 11685767) and OD was measured after 30-60 min at 405 nm with an ELISA reader.

Example 3

Study I: Study Population

In a first study, samples derived from 56 well-characterized LC patients with the UICC classification given in Table 1 have been used. The focus of this cohort was on NSCLC (50 samples), since this form of LC has a better prognosis than the SC type, and thus its early detection is especially important.

TABLE 1

Study I: LC samples and corresponding UICC classification

| Stage according to UICC | Number of samples |
| --- | --- |
| UICC I | 7 |
| UICC II | 17 |
| UICC III | 14 |
| UICC IV | 14 |
| without staging | 4 |
| total number of LC samples | 56 |
| thereof number of NSCLC samples | 50 |
| thereof number of SCLC samples | 6 |

The LC samples of Table 1 have been evaluated in comparison to control samples obtained from 121 obviously healthy individuals without any known malignant lung disease (control cohort).

Example 4

Study I: Sensitivity of Single Markers

Sensitivity for each marker has been calculated at a common specificity level of 95% for each individual marker tested. Table 2 gives the sensitivity in percent for each of the most promising LC markers.

TABLE 2

Study I: Sensitivity of single markers

| marker | NNMT | CEA | NSE | CYFRA 21-1 |
|---|---|---|---|---|
| sensitivity (%) at 95% specificity | 50.0 | 42.9 | 12.5 | 69.6 |

As is readily obvious from Table 2, the marker NNMT has be found to have the second highest sensitivity for LC of all the markers investigated, after CYFRA 21-1. The marker CEA appears to have a significantly lower sensitivity whereas NSE seems to perform rather poor.

Example 5

Study I: Marker Combinations

An individual was classified as having LC if at least one of the markers of the respective combination exceeds a certain threshold. These cut-off values were defined such as to yield 95% specificity on the control cohort.

Table 3 presents the classification results of patients diagnosed with LC versus healthy controls.

TABLE 3

Study I: Classification results on the set of patients with LC versus healthy controls

| No of Markers | Marker or marker panel | Cut-off | Sensitivity (%) |
|---|---|---|---|
| 1 | Cyfra 21-1 | 1.7 ng/ml | 69.6 |
| 1 | NNMT | 884 pg/ml | 50.0 |
| 1 | CEA | 5.5 ng/ml | 42.9 |
| 1 | NSE | 17.7 ng/ml | 12.5 |
| 2 | Cyfra 21-1, CEA | 1.9 ng/ml 5.8 ng/ml | 73.0 |
| 2 | Cyfra 21-1 NNMT | 1.9 ng/ml 970 pg/ml | 77.0 |
| 2 | NNMT, CEA | 1100 pg/ml 6 ng/ml | 66.0 |
| 2 | NNMT NSE | 884 pg/ml 26 ng/ml | 50.0 |
| 3 | NNMT Cyfra 21-1 CEA | 970 pg/ml 1.9 ng/ml 6 ng/ml | 77.0 |

The combination of the markers NNMT and Cyfra 21-1 in this analysis yielded the highest sensitivity at a specificity level of 95%. Various other markers have been evaluated in combination with NNMT. As shown in Table 3, CEA in combination with NNMT also leads to a significant improvement in sensitivity.

Example 6

Study II: Study Population

A second study totally independent from the first one focused on the main types of NSCLC, adenocarcinoma and squamous cell carcinoma. Table 4a describes the type and stage distribution of the cancer cohort.

TABLE 4a

Study II: Type and staging, of LC samples

| | Number of samples | |
|---|---|---|
| Type of Cancer | UICC I or II | UICC III or IV |
| Adenocarcinoma | 12 | 18 |
| Squamous cell carcinoma | 12 | 18 |
| total number of NSCLC samples | 60 | |

The control cohort in this study was defined more specifically to contain samples from smokers and non-smokers as described in Table 4b. A lung function testing (spirometry, Miller, M. R., et al., Eur. Respir. J. 26 (2005) 319-338) was carried out with each individual. Samples were included in the control cohort only if the donor's result in the lung function test was within the normal range.

TABLE 4b

Study II: Composition of the control cohort

| Stage according to UICC | Number of samples |
|---|---|
| Smokers | 30 |
| Ex-smokers | 6 |
| Non-smokers | 24 |

Example 7

Study II: Sensitivity of Single Markers

Sensitivity for each marker has been calculated as before based on the samples described in Table 4b. Sensitivity (in percent) is given at a common specificity level of 95% for each individual marker tested. Table 5 depicts the sensitivity for adenocarcinoma and squamous cell carcinoma, respectively, as well as the overall sensitivity of each of the markers.

TABLE 5

Study II: Sensitivity (%) of single markers at 95% specificity

| marker | NNMT | CEA | NSE | CYFRA 21-1 |
|---|---|---|---|---|
| Adenocarcinoma | 80 | 43 | 37 | 63 |
| Squamous cell carcinoma | 87 | 17 | 30 | 80 |
| Lung cancer overall | 83 | 30 | 33 | 72 |

Clearly, in this case NNMT is superior to Cyfra 21-1 for two reasons: Firstly the overall sensitivity of NNMT is significantly better. Secondly and also very importantly, Cyfra 21-1 is indicating adenocarcinomas with less efficiency than squamous cell carcinomas, whereas NNMT performs similarly with both types of cancer.

Example 8

Study II: Marker Combinations

Results with marker combinations in study II are shown in Table 6. The type of combination was the same as described above for study I.

TABLE 6

Study II: Performance of marker combinations on two major subtypes of lung cancer.

| Marker or marker set #, respectively | Marker or marker panel | Cut-off | Sensitivity (%) | | |
|---|---|---|---|---|---|
| | | | Adeno-carcinoma | Squamous cell carcinoma | Lung cancer overall |
| 1 | Cyfra 21-1 | 2.1 ng/ml | 63 | 80 | 72 |
| 2 | NNMT | 438 pg/ml | 80 | 87 | 83 |
| 3 | CEA | 5.6 ng/ml | 43 | 17 | 30 |
| 4 | NSE | 14.6 ng/ml | 37 | 30 | 33 |
| 5 | Cyfra 21-1, CEA | 2.1 ng/ml 9.2 ng/ml | 80 | 80 | 80 |
| 6 | Cyfra 21-1 NSE | 2.1 ng/ml 17.3 ng/ml | 70 | 80 | 75 |
| 7 | Cyfra 21-1 NNMT | 2.1 ng/ml 520 pg/ml | 83 | 90 | 87 |
| 8 | NNMT, CEA | 438 pg/ml 9.2 ng/ml | 93 | 87 | 90 |
| 9 | NNMT NSE | 438 pg/ml 17.3 ng/ml | 83 | 90 | 87 |
| 10 | NNMT Cyfra 21-1 CEA | 520 pg/ml 2.1 ng/ml 9.2 ng/ml | 97 | 90 | 93 |
| 11 | NNMT Cyfra 21-1 NSE | 520 pg/ml 2.1 ng/ml 17.3 ng/ml | 87 | 90 | 88 |
| 12 | NNMT CEA NSE | 438 pg/ml 9.2 ng/ml 17.3 ng/m | 93 | 90 | 92 |
| 13 | Cyfra 21-1 CEA NSE | 2.1 ng/ml 9.2 ng/ml 17.3 ng/m | 83 | 80 | 82 |
| 14 | NNMT Cyfra 21-1 CEA NSE | 520 pg/ml 2.1 ng/ml l 9.2 ng/ml 17.3 ng/m | 97 | 90 | 93 |

Sensitivity given at 95% specificity

Combining any two of the markers investigated leads to significant improvement in sensitivity of the marker combination as compared to the sensitivity obtained when using the markers individually (see marker sets #7 vs. #1 and #2 for illustration). Some benefit is gained by adding a third marker (cf. sets #8 vs #10). The combination of all four markers (set #14), however, yields no higher performance than the best triple set (set #10).

Dual and triple combinations comprising NNMT are always better than the corresponding ones having NNMT replaced with any other marker.

In summary, NNMT alone demonstrates good sensitivity in detecting the two major types of NSC lung cancer. Very impressive results are obtained using a combination of NNMT with Cyfra 21-1 and/or CEA, respectively. Using a combination comprising all three markers 93% of cancer samples and 95% of controls are classified correctly.

What is claimed is:

1. A method for assessing a presence of lung cancer in a patient comprising the steps of
    measuring in a sample from the patient a level of nicotinamide N-methyl transferase (NNMT), and
    comparing the level of NNMT measured with a level of NNMT in healthy individuals and using the comparison in assessing the presence of lung cancer in the patient.

2. The method according to claim 1, further comprising the steps of measuring in the sample a level of a marker selected from the group consisting of soluble 30 kDa fragment of cytoceratin 19 (CYFRA 21-1), carcinoembryogenic antigen (CEA), neuron-specific enolase (NSF), and squamous cell carcinoma antigen (SCC) and comparing the level of the marker measured with a level of the marker in healthy individuals and using the comparison of the marker and the comparison of the NNMT in assessing lung cancer in the patient.

3. The method according to claim 2, wherein said marker is CYFRA 21-1.

4. The method according to claim 2, wherein said marker is CEA.

5. The method according to claim 2, wherein said marker is SCC.

6. The method according to claim 1 wherein the sample is selected from the group consisting of whole blood, serum, plasma, bronchial lavage, and sputum.

* * * * *

```
SEQUENCE LISTING

<160> NUMBER OF SEQ ID NOS: 1

<210> SEQ ID NO 1
<211> LENGTH: 264
<212> TYPE: PRT
<213> ORGANISM: Homo sapiens

<400> SEQUENCE: 1

Met Glu Ser Gly Phe Thr Ser Lys Asp Thr Tyr Leu Ser His Phe Asn
1               5                   10                  15

Pro Arg Asp Tyr Leu Glu Lys Tyr Tyr Lys Phe Gly Ser Arg His Ser
            20                  25                  30

Ala Glu Ser Gln Ile Leu Lys His Leu Leu Lys Asn Leu Phe Lys Ile
        35                  40                  45

Phe Cys Leu Asp Gly Val Lys Gly Asp Leu Leu Ile Asp Ile Gly Ser
```

-continued

```
                50                   55                   60
Gly Pro Thr Ile Tyr Gln Leu Leu Ser Ala Cys Glu Ser Phe Lys Glu
 65                   70                   75                   80

Ile Val Val Thr Asp Tyr Ser Asp Gln Asn Leu Gln Glu Leu Glu Lys
                  85                   90                   95

Trp Leu Lys Lys Glu Pro Glu Ala Phe Asp Trp Ser Pro Val Val Thr
             100                  105                  110

Tyr Val Cys Asp Leu Glu Gly Asn Arg Val Lys Gly Pro Glu Lys Glu
             115                  120                  125

Glu Lys Leu Arg Gln Ala Val Lys Gln Val Leu Lys Cys Asp Val Thr
             130                  135                  140

Gln Ser Gln Pro Leu Gly Ala Val Pro Leu Pro Pro Ala Asp Cys Val
145                  150                  155                  160

Leu Ser Thr Leu Cys Leu Asp Ala Ala Cys Pro Asp Leu Pro Thr Tyr
                 165                  170                  175

Cys Arg Ala Leu Arg Asn Leu Gly Ser Leu Leu Lys Pro Gly Gly Phe
             180                  185                  190

Leu Val Ile Met Asp Ala Leu Lys Ser Ser Tyr Tyr Met Ile Gly Glu
             195                  200                  205

Gln Lys Phe Ser Ser Leu Pro Leu Gly Arg Glu Ala Val Glu Ala Ala
         210                  215                  220

Val Lys Glu Ala Gly Tyr Thr Ile Glu Trp Phe Glu Val Ile Ser Gln
225                  230                  235                  240

Ser Tyr Ser Ser Thr Met Ala Asn Asn Glu Gly Leu Phe Ser Leu Val
                 245                  250                  255

Ala Arg Lys Leu Ser Arg Pro Leu
             260
```